(12) United States Patent
Kumar

(10) Patent No.: US 10,743,865 B1
(45) Date of Patent: Aug. 18, 2020

(54) APPARATUS FOR SUBCUTICULAR SUTURING AND CORRESPONDING METHOD OF USE THEREOF

(71) Applicant: Sarbjeet S. Kumar, Springfield, TN (US)

(72) Inventor: Sarbjeet S. Kumar, Springfield, TN (US)

( * ) Notice: Subject to any disclaimer, the term of this patent is extended or adjusted under 35 U.S.C. 154(b) by 0 days.

(21) Appl. No.: 16/678,736

(22) Filed: Nov. 8, 2019

Related U.S. Application Data

(63) Continuation of application No. 16/202,648, filed on Nov. 28, 2018, now Pat. No. 10,499,907.

(51) Int. Cl.
  *A61B 17/062* (2006.01)
  *A61B 17/06* (2006.01)
  *A61B 17/00* (2006.01)

(52) U.S. Cl.
  CPC .... *A61B 17/0625* (2013.01); *A61B 17/06061* (2013.01); *A61B 17/06166* (2013.01); *A61B 17/06114* (2013.01); *A61B 2017/0042* (2013.01); *A61B 2017/00469* (2013.01); *A61B 2017/00477* (2013.01)

(58) Field of Classification Search
  CPC .... A61M 5/001; A61M 5/329; A61M 5/3273; A61M 25/0612; A61B 17/0482; A61B 17/0493; A61B 17/0625; A61B 2017/06142; A61B 5/15074; A44C 7/001; D05B 55/00; D05B 15/20; D05B 85/00; D05B 91/00; A41H 37/008
  See application file for complete search history.

(56) References Cited

U.S. PATENT DOCUMENTS

| | | | | |
|---|---|---|---|---|
| 2,814,296 A | * | 11/1957 | James | A61B 17/06 604/265 |
| 3,206,086 A | * | 9/1965 | Duffney | D05B 85/00 223/102 |
| 3,877,570 A | * | 4/1975 | Barry | A61B 17/06133 206/63.3 |
| 5,100,431 A | * | 3/1992 | Buster | A61B 17/06004 606/222 |
| 5,741,299 A | * | 4/1998 | Rudt | A61B 17/0493 606/224 |
| 5,984,932 A | * | 11/1999 | Yoon | A61B 17/0469 606/147 |
| 6,264,675 B1 | * | 7/2001 | Brotz | A61B 17/00491 606/216 |

(Continued)

*Primary Examiner* — Anh T Dang
(74) *Attorney, Agent, or Firm* — Patterson Intellectual Property Law, P.C.; Alex H. Huffstutter

(57) ABSTRACT

An apparatus capable of and a corresponding method for subcuticular suturing of an incision in a single pass is provided. The apparatus includes a straight needle, a suture thread extending from a free end of the needle, and a grip couplable to or pre-attached to the needle. The grip is used for controlling, manipulating, and advancing the needle and its sharp end through the incision. The needle is generally long enough to pierce and bind both sides of the incision together without having to pull the entire needle and any slack in the suture thread through each piercing prior to proceeding to the next piercing. The needle holds the entire incision closed presets the entire path for the suture thread prior to pulling the suture thread through the incision to hold the incision closed.

18 Claims, 10 Drawing Sheets

(56) References Cited

U.S. PATENT DOCUMENTS

| | | | |
|---|---|---|---|
| 2006/0135995 A1* | 6/2006 | Ruff | A61L 17/04 |
| | | | 606/228 |
| 2006/0213232 A1* | 9/2006 | Diana | D04B 3/02 |
| | | | 66/1 A |
| 2008/0039871 A1* | 2/2008 | Wallace | A61B 17/0469 |
| | | | 606/139 |
| 2017/0196552 A1* | 7/2017 | Endo | A61B 17/06004 |

* cited by examiner

APPARATUS FOR SUBCUTICULAR SUTURING AND CORRESPONDING METHOD OF USE THEREOF

CROSS-REFERENCES TO RELATED APPLICATIONS

This application is a continuation application of U.S. Non-Provisional patent application Ser. No. 16/202,648 filed Nov. 28, 2018, entitled "Apparatus for Subcuticular Suturing and Corresponding Method of Use Thereof."

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

BACKGROUND

1. Field of the Invention

The present disclosure relates generally to medical devices and a corresponding method of use. More particularly, this disclosure pertains to suturing needles for closing the two sides of an incision or cut in human skin or other body tissue.

2. Description of the Prior Art

There are at least three commonly known and used methods for closing incisions or open wounds. All three are well known in the prior art. The first is conventional stitches. Conventional stitches have several problems such as leaving a poor scar and that they must be removed later. The second is skin staples. Skin staples have the same problems as those associated with conventional stitches. Conventional stitches, usually, and staples are placed as single interrupted units. And finally, the third is subcuticular sutures, which are usually placed in a continuous running manner. Subcuticular sutures generally leave better scars than the previous two methods because these do not puncture through the skin surface but lie under the skin surface. Furthermore, subcuticular sutures are positioned under the skin and are absorbable, thus they don't need to be removed. Subcuticular sutures are the closure of choice used by most plastic surgeons. Subcuticular suturing, however, may take substantially more time to implement than conventional stitches or skin staples. Accordingly, subcuticular sutures do not get used as often as the conventional stitches or skin staples.

Subcuticular suturing requires the excess suture material to be pulled through after each pass of the needle (i.e., after each stitch). A pass of the needle may be defined as the entire needle passing through the undersurface of the skin. The requirement of pulling all excess suture material after each pass of the needle, associated with each respective method, adds considerable time to the process of closing incisions and open wounds.

Each of the conventional stitching and the subcuticular suturing methods are implemented using small gauge needles. These small gauge needles may be hard to grip, manipulate, and advance through skin that is sometimes dense and difficult to penetrate.

BRIEF SUMMARY

Accordingly, a need exists for an improvement in the conventional method of subcuticular suturing and for gripping, manipulating, and advancing needles through a patient's skin while closing incisions or open wounds. It is one object of the present disclosure to provide a grip configured to be attached to a needle for subcuticular suturing. The grip makes it easier for a surgeon to grasp, manipulate, and advance the needle through incisions or open wounds. An elongated straight suture needle allows for a one pass subcuticular suturing method. The grip in combination with the elongated needle makes the new method easier and faster to implement than previous conventional stitching and suturing methods.

According to one aspect of the present disclosure, there is provided an apparatus for subcuticular suturing. The apparatus is comprised of a needle and a removable grip. The needle has a distal portion and a proximal portion. The distal portion is sharp. The removable grip is couplable to the needle closer to the proximal portion than to the distal portion.

According to another aspect of the apparatus of the present disclosure, the proximal portion of the needle may include a suture thread extending from a free end of the proximal portion.

According to another aspect of the apparatus of the present disclosure, the grip may be configured to be held between the fingers of a user.

According to another aspect of the present disclosure, the needle may be straight.

According to another aspect of the apparatus of the present disclosure, the needle may have a length of at least six inches.

According to another aspect of the apparatus of the present disclosure, the grip may be repositionable on the needle between the proximal portion and the distal portion.

According to another aspect of the apparatus of the present disclosure, the grip may be coupled to the proximal portion of the needle.

According to further aspects of the present disclosure, there is provided a method of subcuticular suturing of an incision through skin, the incision having a first side, a second side, a first end, a second end, and a length. The method comprises: step (a) providing a needle having a sharp distal portion and a proximal portion with a suture extending therefrom; step (b) inserting the sharp distal portion of the needle through the skin or through a first subcuticular portion of the skin proximate to the first end of the incision; step (c) piercing the first side of the incision with the sharp distal portion; step (d) piercing the second side of the incision with the sharp distal portion; step (e) pushing the sharp distal portion through the skin or through a second subcuticular portion of the skin proximate to the second end of the incision; and step (f) pulling the needle and the suture through the incision.

According to another aspect of the method of the present disclosure, step (a) may include providing a plastic tab configured to be attached to the needle; step (a) may further include attaching the plastic tab to a first selected location of the needle between the sharp distal portion and the proximal portion; and steps (b-e) may further include manipulating the plastic tab to control and advance the sharp distal portion.

According to another aspect of the method of the present disclosure, any of steps (b-e) may further include repositioning the plastic tab to a second location of the needle. The second location of the needle may be closer to the proximal portion than the first location.

According to another aspect of the method of the present disclosure, step (f) may include removing the plastic tab from the needle prior to pulling the needle and the suture through the incision.

According to another aspect of the method of the present disclosure, step (a) may further include providing a plastic tab attached to the proximal portion of the needle; steps (b-e) may further include manipulating the plastic tab to control and advance the sharp distal portion; and step (f) may further include breaking the plastic tab off of the needle prior to pulling the needle and the suture through the incision.

According to another aspect of the method of the present disclosure, the method may further comprise separating the needle from the suture, and tying a first knot in the suture proximate to the first end of the incision and tying a second knot in the suture proximate to the second end of the incision.

According to another aspect of the method of the present disclosure, the method may further comprise repeating step (c) and step (d) until the sharp distal portion of the needle reaches the second end of the incision.

According to another aspect of the method of the present disclosure, the provided needle in step (a) has a length greater than the length of the incision.

According to another aspect of the method of the present disclosure, the method prior to step (a) may further comprise providing a sterilized and sealed kit containing a plastic tab and the needle with the suture extending from the needle, removing the plastic tab and the needle from the kit, and attaching the plastic tab to the proximal portion of the needle.

According to still further aspects of the present disclosure, there is provided a kit for suturing an incision in the skin. The kit comprises a sterilized and sealed container, a needle, a suture thread, and a removable handle. The sterilized and sealed container is configured to contain the needle, the suture thread, and the removable handle. The needle has a sharp distal portion and a proximal portion. The suture thread is configured to couple to and extend from the proximal portion of the needle. The removable handle is couplable to the needle between the proximal portion and the sharp distal portion.

According to another aspect of the kit of the present disclosure, the handle is configured to be gripped between multiple fingers of a user.

According to another aspect of the kit of the present disclosure, the needle is generally straight and has a length that ranges between four and eight inches.

According to another aspect of the kit of the present disclosure, the suture thread comes pre-attached to the proximal end of the needle.

According to another aspect of the kit of the present disclosure, the handle comes pre-attached to the proximal end of the needle and is removable by snapping the handle off.

The invention, together with additional features and advantages thereof, may best be understood by reference to the following description taken in connection with the accompanying illustrative drawing.

DETAILED DESCRIPTION

Reference will now be made in detail to embodiments of the present disclosure, one or more drawings of which are set forth herein. Each drawing is provided by way of explanation of the present disclosure and is not a limitation. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

Thus, it is intended that the present disclosure covers such modifications and variations as come within the scope of the appended claims and their equivalents. Other objects, features, and aspects of the present disclosure are disclosed in, or are obvious from, the following detailed description. It is to be understood by one of ordinary skill in the art that the present discussion is a description of exemplary embodiments only and is not intended as limiting the broader aspects of the present disclosure.

The words "connected", "attached", "joined", "mounted", "fastened", and the like should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Unless specifically stated otherwise, any part of the apparatus of the present disclosure may be made of any appropriate or suitable material including, but not limited to, metal, alloy, polymer, polymer mixture, wood, composite, or any combination thereof.

Figure 1:
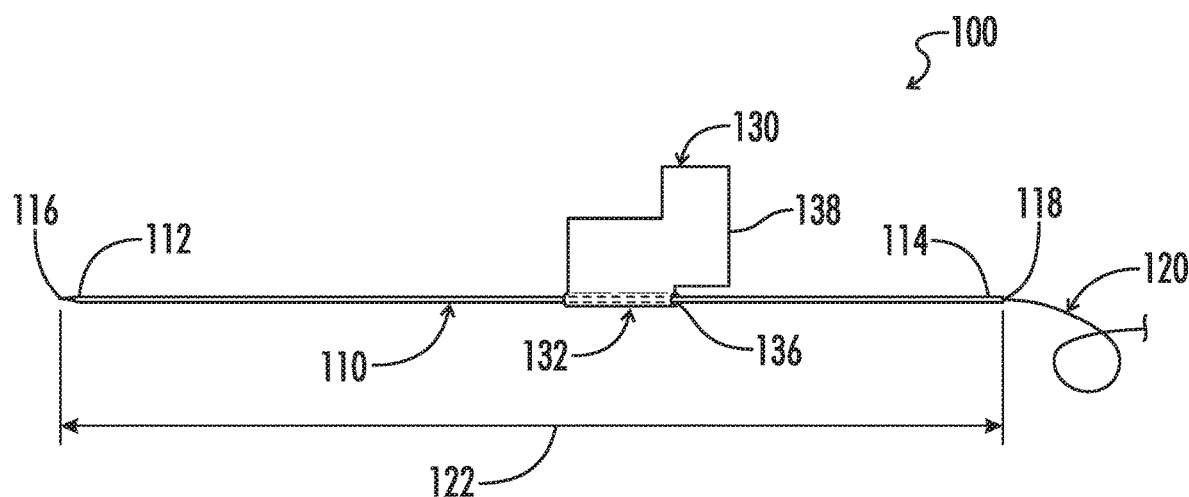
FIG. 1 illustrates a perspective view of an exemplary embodiment of an apparatus for subcuticular suturing with a plastic tab in a first position in accordance with the present disclosure.
Figure 2:
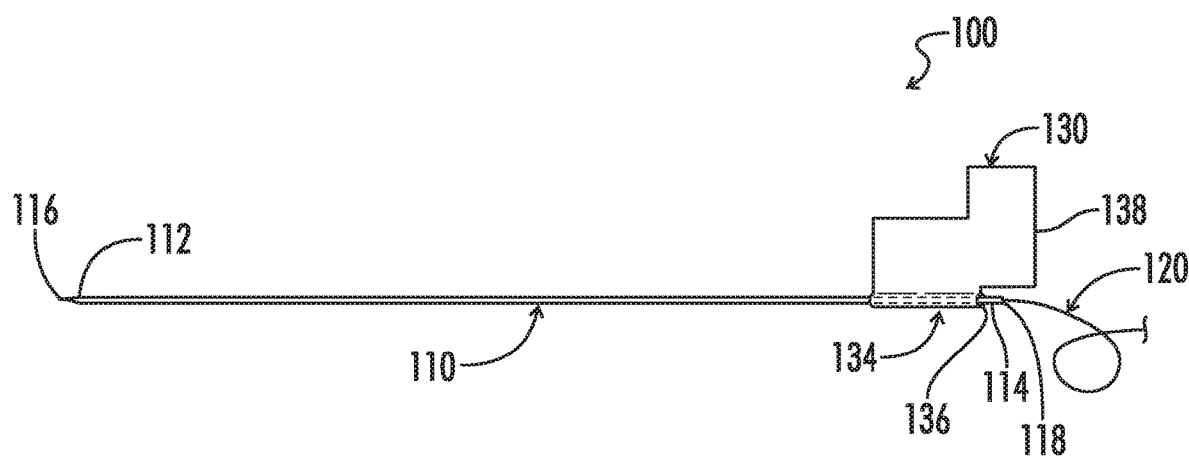
FIG. 2 illustrates a perspective view of the apparatus of FIG. 1 with the plastic tab in a second position.
Figure 3:
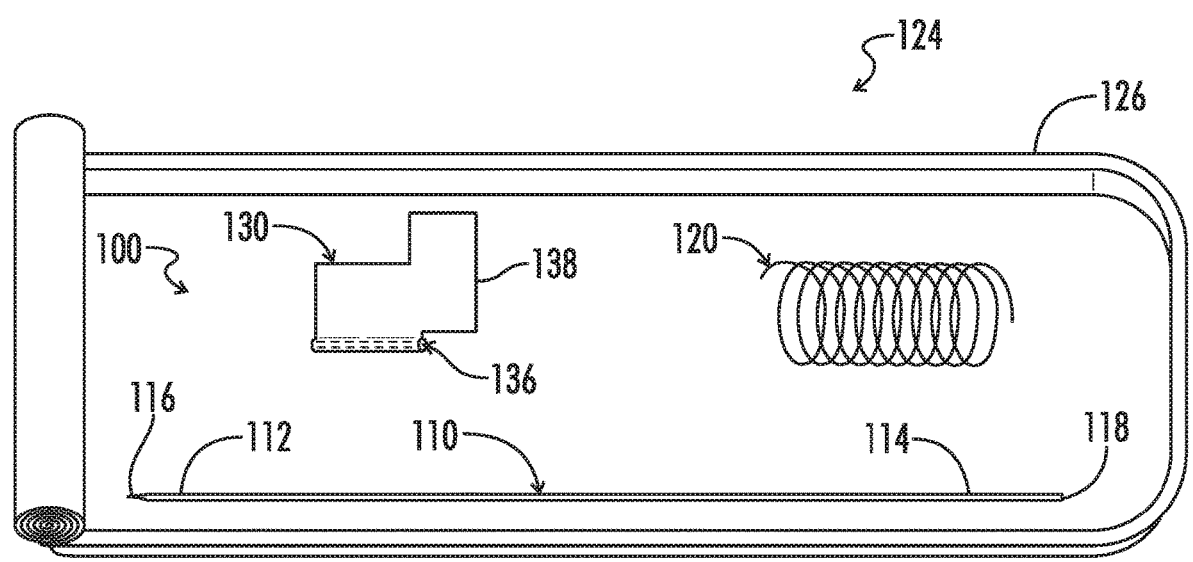
FIG. 3 illustrates an exploded perspective view of the apparatus of FIG. 1 positioned inside a containment sleeve.

Referring to FIGS. 1-3, an apparatus 100 for performing a subcuticular suture in a single pass is provided. The apparatus 100 includes a needle 110 and a removable grip 130. The grip 130 may also be referred to herein as a plastic tab 130 or a handle 130. The grip 130 is attached to the needle 110 and is configured to be gripped between multiple fingers (not shown) of a surgeon (not shown). The surgeon may also be referred to herein as a physician or a user. The grip 130 advantageously aids the surgeon in manipulating and advancing the needle 110 through an incision 200 in skin 202. The incision 200 may be referred to herein as a wound 200 or an open wound 200. The apparatus 100 may be used to perform subcuticular suturing in a single pass because the needle 110 is not pulled completely through after each piercing or puncture, but instead remains in each piercing or puncture until the incision is closed along the needle 110.

The needle 110 has a distal portion 112 and a proximal portion 114. The distal portion 112 of the needle 110 may include a sharp end 116. The distal portion 112 may also be referred to herein as a sharp distal portion 112. The proximal portion 114 may include a free end 118. The free end 118 of the proximal portion 114 may be configured to have a suture thread 120 extend from a hole (not shown) of the free end 118. The suture thread 120 may also be referred to herein as a suture 120 or a suture material 120. The suture thread 120 may be any suitable type of material. The type of suture material is generally an absorbable type such as vicryle, monocryl, gut, collagen, or the like. Furthermore, the needle 110 may come with the suture thread 120 pre-attached to the free end 118 of the proximal portion 114.

The needle 110 is straight and has a length 122 defined between the sharp end 116 and the free end 118. In other embodiments (not shown), the needle 110 may be shaped differently such as curved. The length 122 of the needle may be at least 6 inches long. Ideally, the needle 110 should be slightly longer than an incision 200 (FIGS. 4-10). Generally, a needle 110 with length 122 between four (4") inches and eight (8") inches long will be sufficiently long for most incisions 200. A needle 110 shorter than the incision will also work but will require a second pass through the incision 200. It is contemplated that the length 122 of the needle 110 may be shorter than four inches in some embodiments and longer than eight inches in other embodiments.

As can best be seen in FIG. 3, the apparatus 100 may be sold in a sterilized and sealed kit 124. The kit includes the needle 110 with suture thread 120 extending from the free end 118, and the grip 130. The kit 124 may be defined as the needle 110, the suture thread 120, and the grip 130, all pre-sterilized and contained in a sealed containment sleeve 126. It is contemplated that multiple kits 124 may be produced, the sealed containment sleeve 126 of each labeled with the length 122 of the needle 110 contained therein.

As can best be seen in FIGS. 1-2, the grip 130 may be coupled to the needle 110 between the distal portion 112 and the proximal portion 114. As shown, the grip 130 is removable and comes as part of the kit 124 (FIG. 3) detached from the needle 110. Furthermore, as shown, the grip 130 is configured to be repositionable on the needle 110. In certain embodiments, the grip 130 is positioned closer to the proximal end 114 than to the distal end 112 of the needle 110. FIG. 1 shows the grip 130 connected to the needle 110 at a first selected location 132, and FIG. 2 shows the grip 130 connected to the needle 110 at a second selected location 134. As shown, the second selected location 134 is closer to the proximal portion 114 than the first selected location 132. The second selected location 134 may be the proximal portion 114 of the needle 110.

The grip 130 includes a clampable passageway 136 for receiving the needle 110 and securely and selectively grasping the needle 110. The passageway 136 may include a non-slip material (not shown) disposed on an inner surface (not shown) of the passageway 136 to ensure that the needle 110 when received by the passageway 136 does not move. The grip 130 may clamp to the needle 110 using any available means to tighten the passageway 136 around the needle 110 such as a ratchet clamp system, a spring clamp system, a toothed clamp system, or the like. As shown, the needle 110 is inserted into the passageway 136, positioned, and clamped in position. Alternatively (now shown), the passageway 136 may be a spring assisted jaw clip configured to open and grab onto any portion of the needle 110 without having to insert the needle 110 through the passageway 136. The grip 130 should be interpreted to include any attachment to a needle 110 for suturing that aids a surgeon in his or her control, manipulation, and advancement of the needle 110, and that also must be removed prior to the needle 110 passing through each puncture and/or completely through the incision 200.

In other embodiments (not shown), the grip 130 may come pre-attached to a location on the needle 100 such as the proximal portion 114 (FIG. 2) of the needle 110. In this embodiment, the grip 130 must be broken off to remove the grip 130 from the needle 110 and the grip 130 may not be reused.

As shown, the grip 130 may include a gripping portion 138 shaped to extend planarly from the needle 110. The gripping portion 138 is configured to be held between multiple fingers (not shown) of the surgeon (not shown). In other embodiments (not shown), the gripping portion 138 may be shaped differently, for example, it may include ergonomic finger divots, and/or it may be shaped other than planar. The size of the grip 130 may either be one size fits all or may come in multiple sizes with the size matched to the length 122 of the needle 110. Furthermore, the size and shape of the gripping portion may be customizable based on physician preferences.

Ideally, the gripping portion 138 should not extend from greater than one-half of the circumference of the needle 110 or that of the passageway 136 so that the needle 110 may be able to lie substantially flat or parallel to the skin 202 adjacent to the incision 200. This ensures that the needle 110 is substantially parallel with an elevation of the incision 200 and is not held away from the skin 202 by the grip 130 while the incision 200 is being sutured.

Referring now to FIGS. 4-10, a method of subcuticular suturing of an incision 200 through skin 202 in a single pass is shown. The method is possible in a single pass when the length 122 of the needle 110 is longer than a length 204 of the incision 200. At least one additional pass may be required when the incision 200 is longer than the needle 110. Even with an additional pass, the method of using the apparatus 100 is still faster and provides better scarring results than conventional stitching. The incision 200 has a first side 206 and a second side 208 that must be brought together to close the incision 200. The first side 206 may also be referred to herein as a first subcuticular side 206 or a first subcuticular side wall 206. The second side 208 may also be referred to herein as a second subcuticular side 208 or a second subcuticular side wall 208.

The method comprises the following steps.

As shown in FIGS. 1-3, the method includes step (a) providing the needle 110 having the sharp distal portion 112 and the proximal portion with a suture thread 120 extending therefrom.

Figure 4:
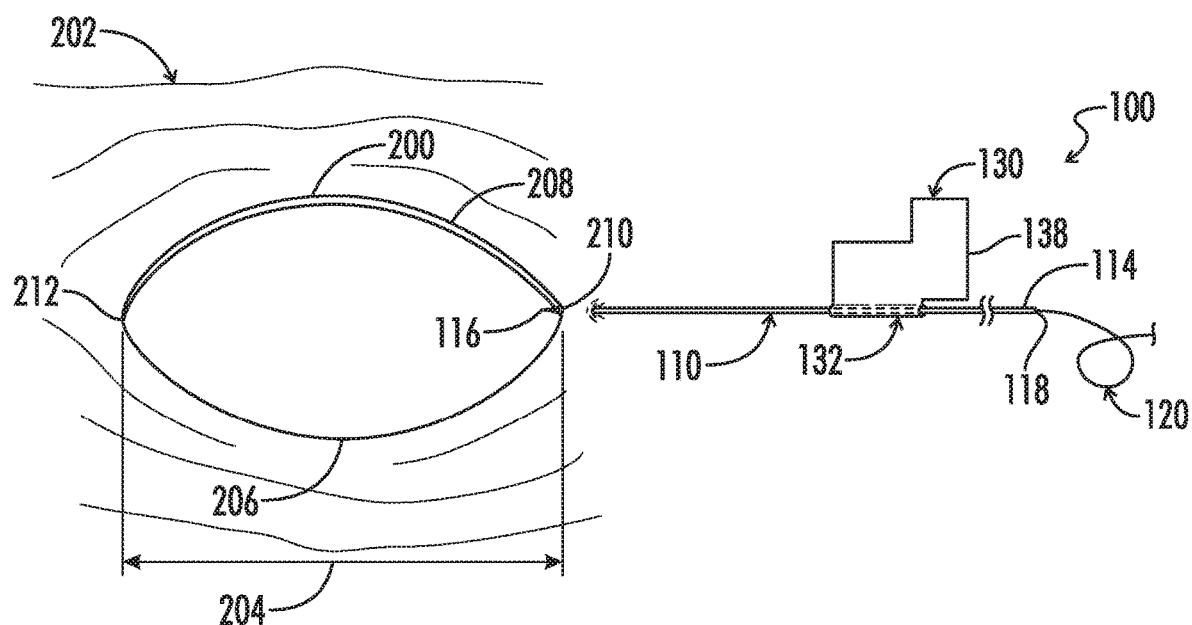
FIG. 4 illustrates a perspective view of the apparatus of FIG. 1 in combination with an incision in the skin, a sharp distal portion of a needle of the apparatus inserted through the skin proximate to a first end of the incision.
Figure 11:
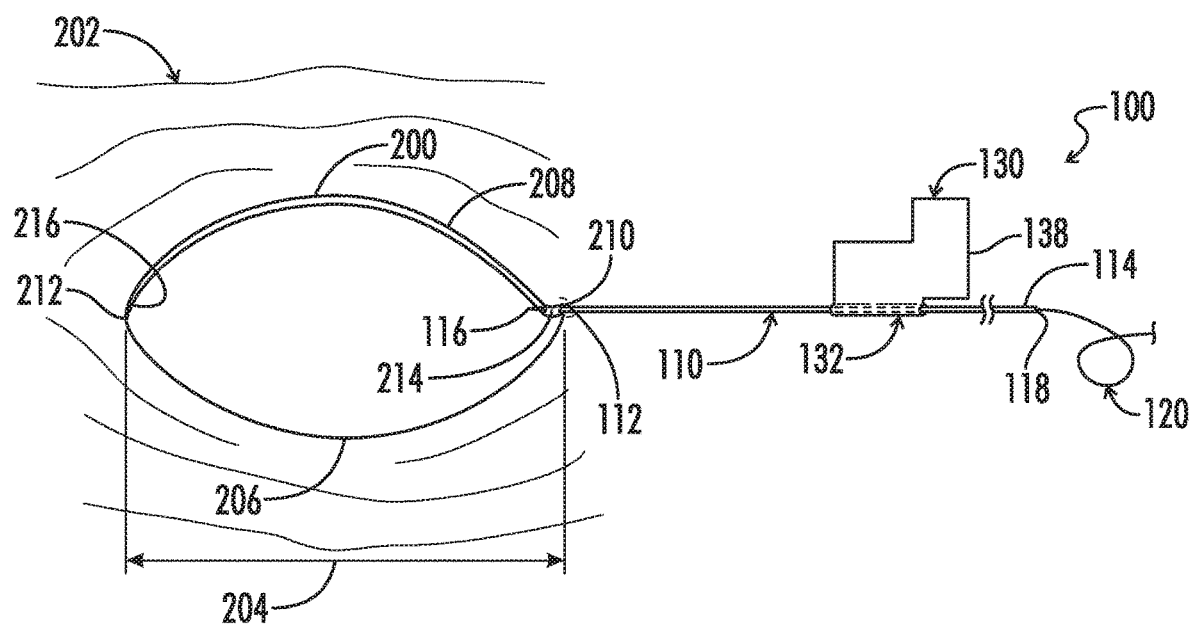
FIG. 11 illustrates a perspective view of the apparatus of FIG. 1 in combination with an incision in the skin, a sharp distal portion of a needle of the apparatus inserted through a first subcuticular portion of the skin proximate to a first end of the incision.

As shown in FIGS. 4 and 11, the method includes step (b) inserting the sharp distal portion 112 of the needle 110 through the skin 202 (FIG. 4) or through a first subcuticular portion 214 of the skin 202 (FIG. 11) proximate to a first end 210 of the incision 200. The sharp distal portion 112 of the needle 110 may point toward the second end 212 of the incision 200 when it is inserted through the skin 202 or first subcuticular portion 214 proximate to the first end 210 of the incision 200.

Figure 5:
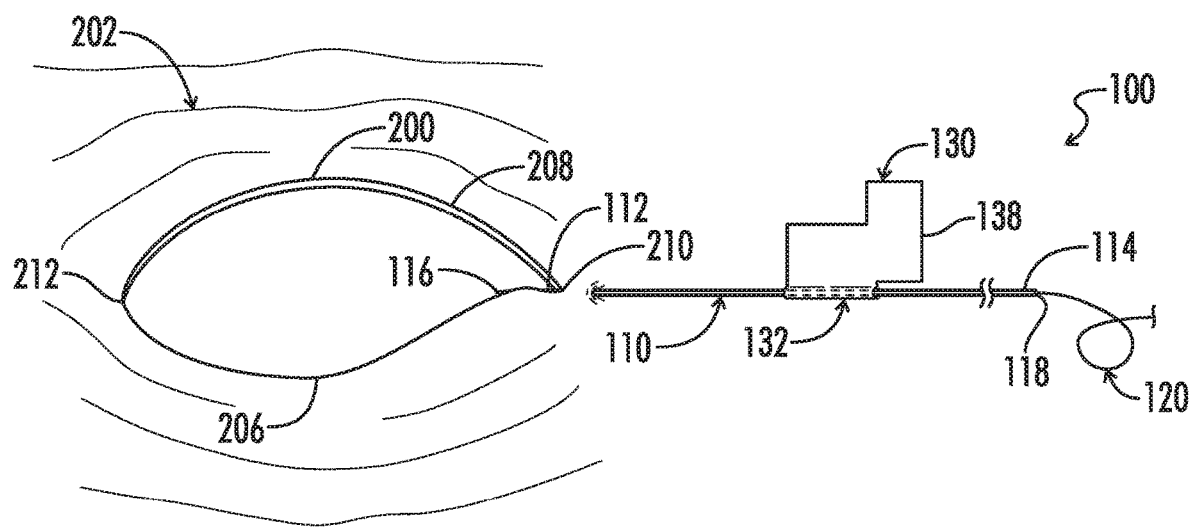
FIG. 5 illustrates a perspective view of the apparatus and incision of FIG. 4 with the sharp distal portion piecing a first side of the incision.
Figure 12:
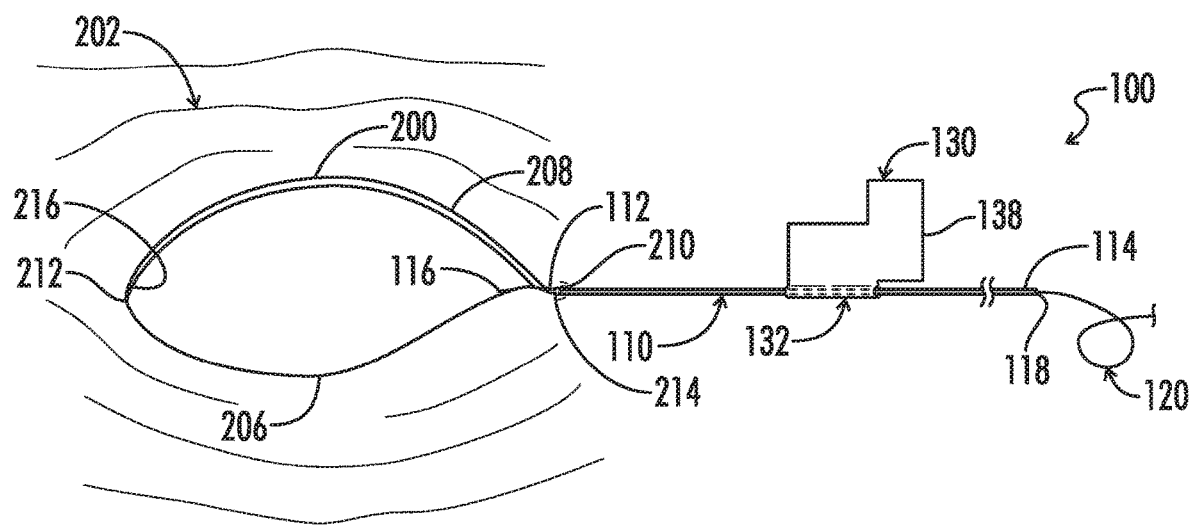
FIG. 12 illustrates a perspective view of the apparatus and incision of FIG. 11 with the sharp distal portion piecing a first side of the incision.

As shown in FIGS. 5 and 12, the method includes step (c) piercing the first side 206 of the incision 200 with the sharp distal portion 112 of the needle 110. To pierce the first side 206 of the incision 200, the skin 202 may have to be manipulated to align the first side 206 with the sharp distal portion 112 of the needle 110.

Figure 6:
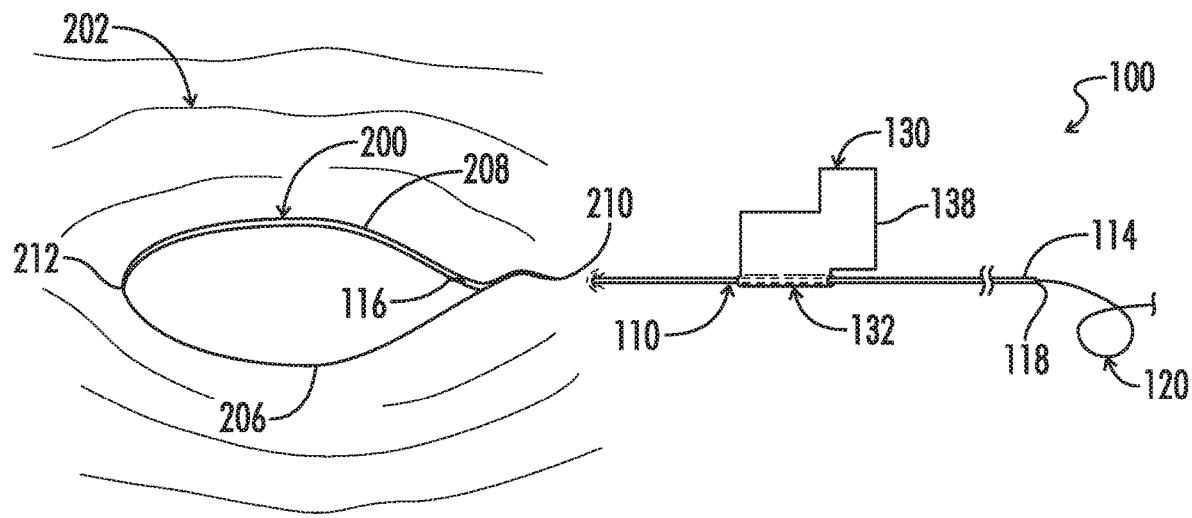
FIG. 6 illustrates a perspective view of the apparatus and incision of FIG. 5 with the sharp distal portion piercing a second side of the incision.
Figure 13:
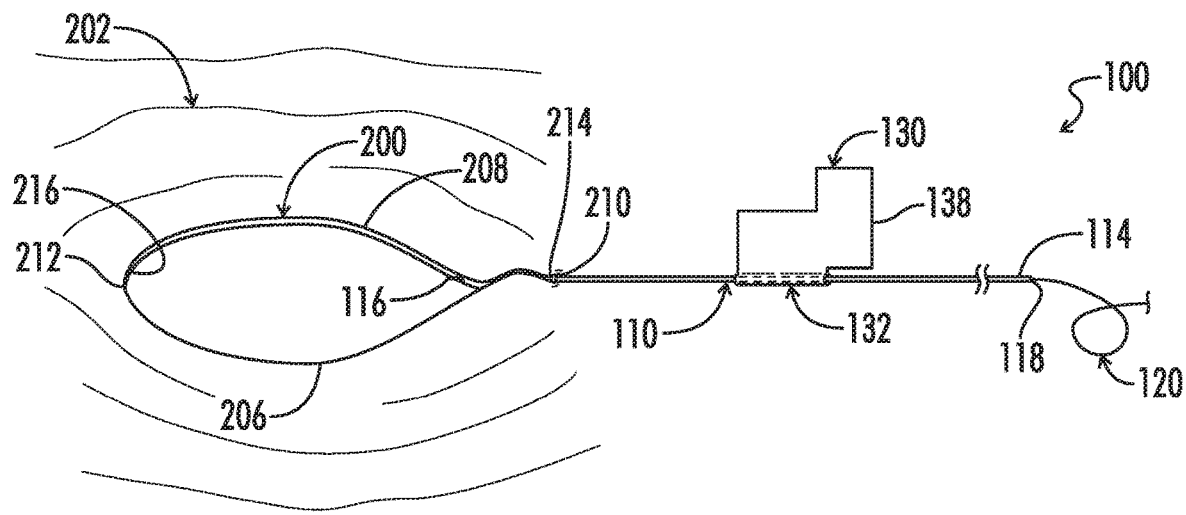
FIG. 13 illustrates a perspective view of the apparatus and incision of FIG. 12 with the sharp distal portion piercing a second side of the incision.

As shown in FIGS. 6 and 13, the method includes step (d) piercing the second side 208 of the incision 200 with the sharp distal portion 112 of the needle 110. Similarly, to pierce the second side 208 of the incision 200, the skin 202 may have to be manipulated to align the second side 208 with the sharp distal portion 112 of the needle 110.

Figure 7:
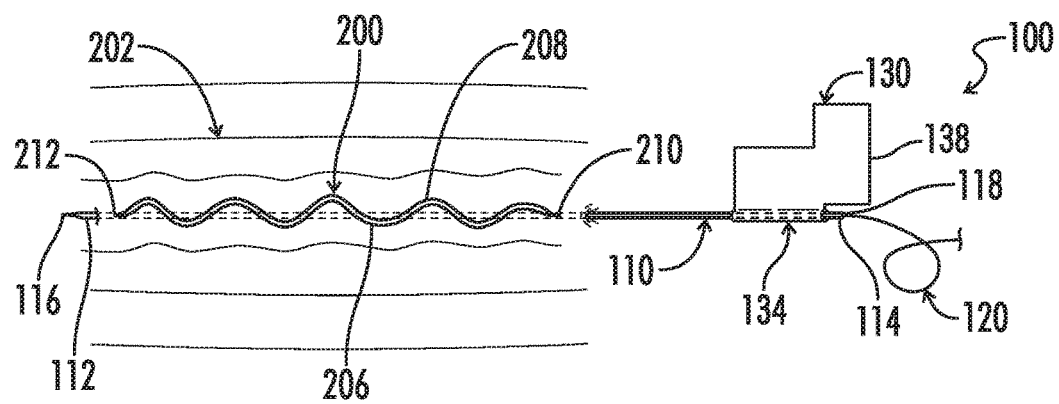
FIG. 7 illustrates a top plan view of the apparatus and incision of FIG. 6 with the sharp distal portion extending through the skin proximate to the second end of the incision.
Figure 14:
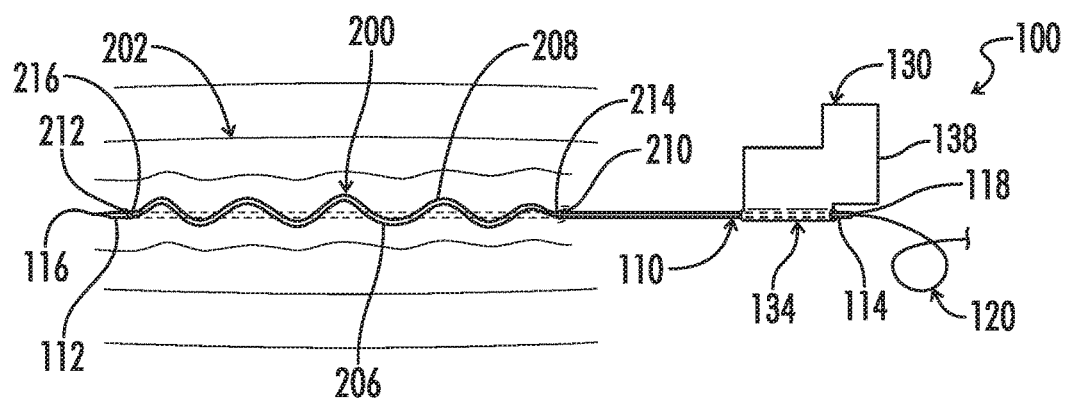
FIG. 14 illustrates a top plan view of the apparatus and incision of FIG. 13 with the sharp distal portion extending through a second subcuticular portion of the skin proximate to the second end of the incision.

As shown in FIGS. 7 and 14, the needle 110 has repeatedly pierced the first 206 and the second side 208 until the second end 212 of the incision 200 is reached. Then the method includes step (e) pushing the sharp distal portion 112 of the needle 110 through the skin 202 (FIG. 7) or through a second subcuticular portion 216 of the skin 202 (FIG. 14) proximate to a second end 212 of the incision 200. As shown in FIG. 7, the sharp distal portion 112 of the needle 110 may extend away from the second end 212 of the incision 200 in a direction away from the first end 210 of the incision 200 when it is pushed through the skin 202 proximate to the second end 212 of the incision 200. As shown in FIG. 14, the sharp distal portion 112 of the needle 110 may extend toward the second end 212 of the incision 200 in a direction away from the first end 210 of the incision 200 when it is pushed through the second subcuticular portion 216 of the skin 202. Any combination of entry and exit points where the needle 110 accesses the incision 200 may be used with this method.

Figure 9:
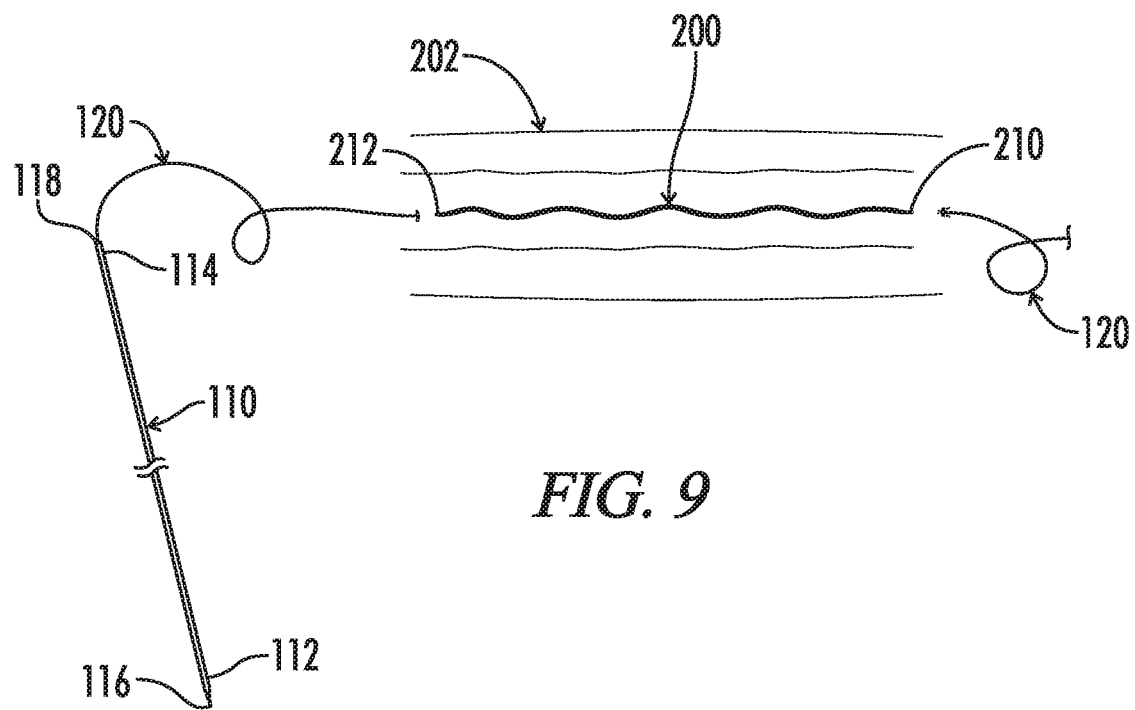
FIG. 9 illustrates a top plan view of the apparatus and incision of FIG. 8 with the needle pulled through the incision and trailing suture thread remaining in the incision.
Figure 16:
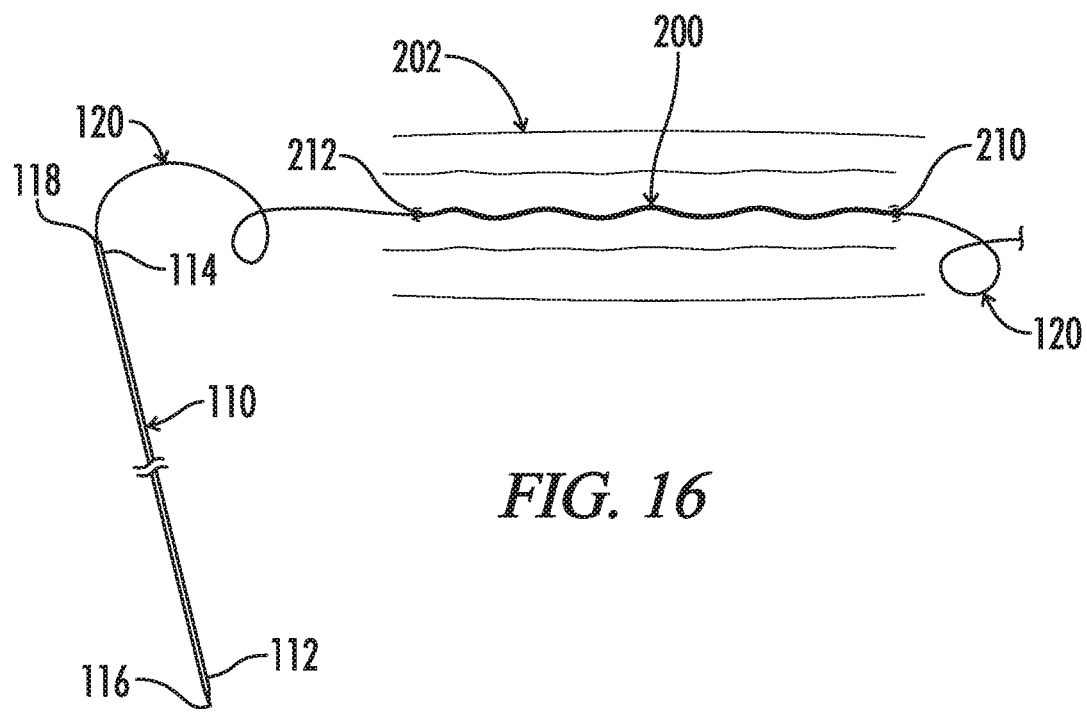
FIG. 16 illustrates a top plan view of the apparatus and incision of FIG. 15 with the needle pulled through the incision and trailing suture thread remaining in the incision.

As shown in FIGS. 9 and 16, the method includes step (f) pulling the needle 110 and the suture thread 120 through the incision 200. The suture thread 120 is attached to and extends from the free end 118 of the proximal portion 114 of the needle 110 and remains in the incision 200 to keep the incision 200 closed.

Figure 10:
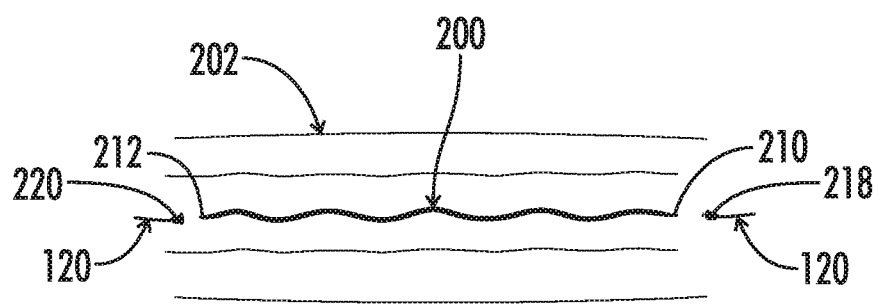
FIG. 10 illustrates a top plan view of the incision of FIG. 9 with suture thread secured.
Figure 17:
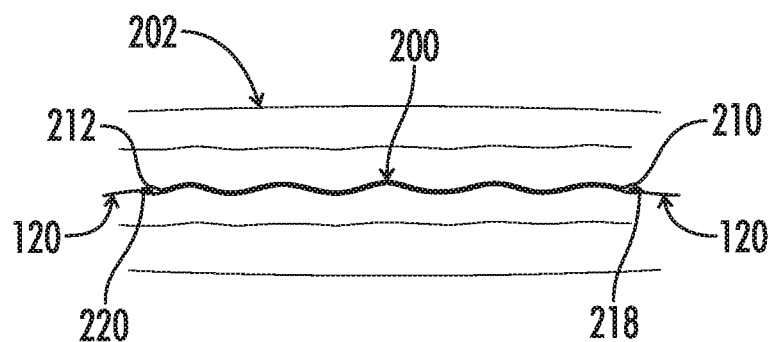
FIG. 17 illustrates a top plan view of the incision of FIG. 16 with suture thread secured.

In certain embodiments as can best be seen in FIGS. 10 and 17, the method may further include separating the needle 110 from the suture thread 120, tying a first knot 218 in the suture thread 120 proximate to the first end 210 of the incision 200, and tying a second knot 220 in the suture thread 120 proximate to the second end 212 of the incision 200. As shown in FIG. 10, the first knot 218 may be tied where the needle 110 originally entered through the skin 202 in step (b), and the second knot 220 may be tied where the needle 110 originally exited through the skin 202 in step (e). As shown in FIG. 17, the first knot 218 may be tied and positioned within the incision 200 where the needle 110 originally entered through the first subcuticular portion 214 of the skin 202 in step (b), and the second knot 220 may be tied and positioned with the incision 200 where the needle 110 originally exited through the second subcuticular portion 216 of the skin 202 in step (e).

In certain embodiments, the method may further comprise sequentially repeating step (c) and step (d) along the length 204 of the incision 200.

In certain embodiments, step (a) of the method may include providing the grip 130 configured to be attached to the needle 110. In accordance with such embodiments, step (a) of the method may further include attaching the grip 130 to the first selected location 132 of the needle 110 between the sharp distal portion 112 and the proximal portion 114. In such embodiments, steps (b-e) of the method may further include manipulating the grip 130 to control and advance the sharp distal portion 112 of the needle 110. Finally, in such embodiments, any of the steps (b-e) may further include repositioning the grip 130 to the second location 134 of the needle 110. It is contemplated that during any of steps (b-e) the grip may be further repositioned to various locations of the needle 110 including any location between the distal portion 112 and the proximal portion 114 and even the proximal portion 114 itself.

Figure 8:
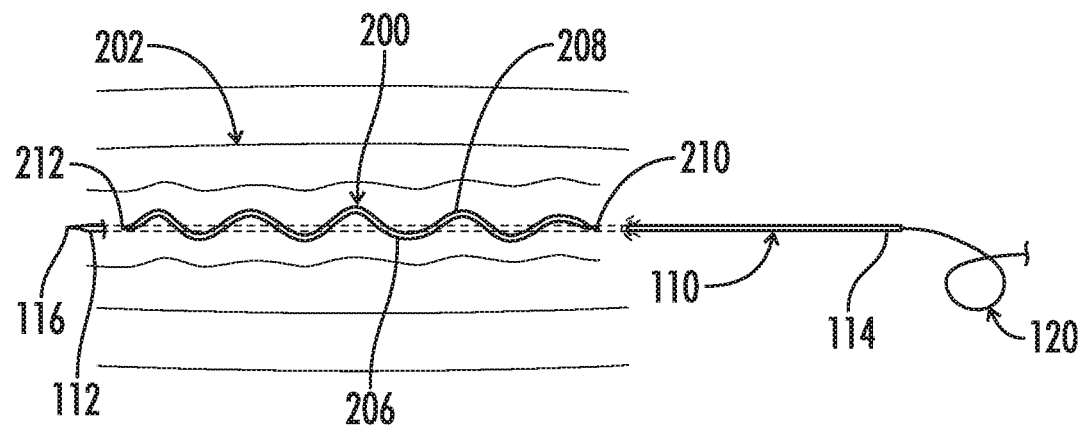
FIG. 8 illustrates a top plan view of the apparatus and incision of FIG. 7 with the plastic tab removed.
Figure 15:
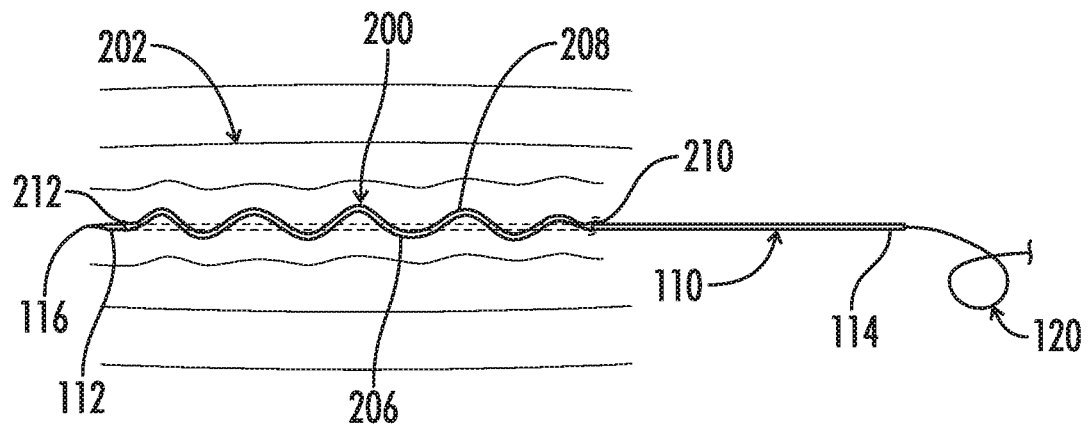
FIG. 15 illustrates a top plan view of the apparatus and incision of FIG. 14 with the plastic tab removed.

As can best be seen in FIGS. 8 and 15, in embodiments of the method where the needle 110 includes the grip 130 coupled thereto, step (f) of the method may include removing the grip 130 from the needle 110 prior to pulling the needle 110 and suture thread 120 through the incision 200. In certain embodiments, the grip 130 may be removed by unclipping it from the needle 110. In other embodiments, the grip 130 may be removed by snapping the grip 130 off of the needle 110.

In certain embodiments, step (a) of the method may include providing the grip 130 pre-attached to the proximal portion 114 of the needle. In accordance with such embodiments, steps (b-e) of the method may include manipulating the grip 130 to control and advance the sharp distal portion 112 of the needle 110. Finally, in accordance with such embodiments, step (f) of the method may include breaking the grip 130 away from the needle 110 prior to pulling the needle 110 and suture thread 120 through the incision 200.

In certain embodiments, the method may further comprise, prior to step (a), providing the sterilized and sealed kit 124 and removing the needle 110 with the suture thread 120 extending therefrom and the grip 130 from the sealed containment sleeve 126 of the kit 124. In accordance with such embodiments, the method may further include attaching the grip to the needle 110 at a location selected by the user (e.g., the surgeon).

The previous detailed description has been provided for the purposes of illustration and description. Thus, although there have been described particular embodiments of a new and useful invention, it is not intended that such references be construed as limitations upon the scope of this invention except as set forth in the following claims.

What is claimed is:

1. A method of subcuticular suturing of an incision through skin, the incision having a first side, a second side, a first end, a second end, and a length defined between the first end and the second end, the method comprising:
   step (a) providing a needle having a sharp distal portion and a proximal portion with a suture extending therefrom;
   step (b) inserting the sharp distal portion of the needle through the skin proximate to the first end of the incision or through a first subcuticular portion of the skin proximate to the first end of the incision;
   step (c) maintaining a portion of the needle in the skin proximate to the first end of the incision or in the first subcuticular portion of the skin proximate to the first end of the incision while performing the following with the needle generally aligned with the length of the incision:
   step (d) piercing the first side of the incision with the sharp distal portion;
   step (e) piercing the second side of the incision with the sharp distal portion; and
   step (f) pushing the sharp distal portion through the skin proximate to the second end of the incision or through a second subcuticular portion of the skin proximate to the second end of the incision; and
   step (g) closing the incision by pulling the sharp distal portion of the needle followed by the proximal portion and the suture through the incision proximate to the second end of the incision.

2. The method of claim 1, wherein:
   step (a) further includes providing a plastic tab configured to be attached to the needle;
   step (a) further includes attaching the plastic tab to a first selected location of the needle between the sharp distal portion and the proximal portion; and
   steps (b-f) further include manipulating the plastic tab to control and advance the sharp distal portion.

3. The method of claim 2, wherein:
   at least one of steps (b-f) further include repositioning the plastic tab to a second location of the needle.

4. The method of claim 2, wherein:
   step (g) includes removing the plastic tab from the needle prior to pulling the needle and the suture through the incision.

5. The method of claim 1, wherein:
   step (a) further includes providing a plastic tab attached to the proximal portion of the needle;
   steps (b-f) further include manipulating the plastic tab to control and advance the sharp distal portion; and
   step (g) includes breaking the plastic tab away from the needle prior to pulling the needle and the suture through the incision.

6. The method of claim 1, further comprising:
   step (h) separating the needle from the suture; and
   step (i) tying a first knot in the suture proximate to the first end of the incision and tying a second knot in the suture proximate to the second end of the incision.

7. The method of claim 1, further comprising sequentially repeating step (d) and step (e) until the sharp distal portion of the needle reaches the second end of the incision to thereby close the incision.

8. The method of claim 1, wherein:
   the provided needle from step (a) has a length greater than the length of the incision.

9. The method of claim 1, further comprising prior to step (a):
   providing a sterilized and sealed kit containing a plastic tab and the needle with the suture extending from the needle;
   removing the plastic tab and the needle from the kit; and
   attaching the plastic tab to a first selected location of the needle between the sharp distal portion and the proximal portion.

10. A method of subcuticular suturing of an incision through skin, the incision having a first side, a second side, a first end, a second end, and a length defined between the first end and the second end, the method comprising:
    step (a) providing a needle having a sharp distal portion and a proximal portion with a suture extending therefrom;
    step (b) inserting the sharp distal portion of the needle through the skin proximate to the first end of the incision or through a first subcuticular portion of the skin proximate to the first end of the incision;
    step (c) maintaining a portion of the needle in the skin proximate to the first end of the incision or in the first subcuticular portion of the skin proximate to the first end of the incision while performing the following:
    step (d) piercing the first side of the incision with the sharp distal portion;
    step (e) piercing the second side of the incision with the sharp distal portion; and
    step (f) pushing the sharp distal portion through the skin proximate to the second end of the incision or through a second subcuticular portion of the skin proximate to the second end of the incision; and
    step (g) closing the incision by pulling the sharp distal portion of the needle followed by the proximal portion and the suture through the incision proximate to the second end of the incision, whereby the entire length of the incision is closed in a single pass of the needle.

11. The method of claim 10, wherein:
    step (a) further includes providing a plastic tab configured to be attached to the needle;
    step (a) further includes attaching the plastic tab to a first selected location of the needle between the sharp distal portion and the proximal portion; and
    steps (b-f) further include manipulating the plastic tab to control and advance the sharp distal portion.

12. The method of claim 11, wherein:
    at least one of steps (b-f) further include repositioning the plastic tab to a second location of the needle.

13. The method of claim 11, wherein:
    step (g) includes removing the plastic tab from the needle prior to pulling the needle and the suture through the incision.

14. The method of claim 10, wherein:
    step (a) further includes providing a plastic tab attached to the proximal portion of the needle;
    steps (b-f) further include manipulating the plastic tab to control and advance the sharp distal portion; and
    step (g) includes breaking the plastic tab away from the needle prior to pulling the needle and the suture through the incision.

15. The method of claim 10, further comprising:
    step (h) separating the needle from the suture; and
    step (i) tying a first knot in the suture proximate to the first end of the incision and tying a second knot in the suture proximate to the second end of the incision.

16. The method of claim 10, further comprising sequentially repeating step (d) and step (e) until the sharp distal portion of the needle reaches the second end of the incision to thereby close the incision.

17. The method of claim 10, wherein:
the provided needle from step (a) has a length greater than the length of the incision.

18. The method of claim 10, further comprising prior to step (a):
providing a sterilized and sealed kit containing a plastic tab and the needle with the suture extending from the needle;
removing the plastic tab and the needle from the kit; and
attaching the plastic tab to a first selected location of the needle between the sharp distal portion and the proximal portion.

\* \* \* \* \*